United States Patent [19]

Kabis

[11] Patent Number: 5,454,275
[45] Date of Patent: Oct. 3, 1995

[54] KABIS DISCRETE GROUNDWATER SAMPLER

[76] Inventor: Thomas W. Kabis, #17 329 S. Hwy. 101, Solana Beach, Calif. 92075

[21] Appl. No.: 247,229

[22] Filed: May 23, 1994

[51] Int. Cl.$^6$ ..................................................... G01N 1/12
[52] U.S. Cl. ...................... 73/864.51; 166/162; 166/264
[58] Field of Search ............ 73/864.51, 864.61–864.67; 166/162, 264

[56] References Cited

U.S. PATENT DOCUMENTS 4,078,433  3/1978  McCabe, Jr. et al. ............... 73/864.61

FOREIGN PATENT DOCUMENTS

| 11336 | 2/1981 | Japan | 73/864.51 |
| 1272151 | 11/1986 | U.S.S.R. | 73/864.51 |
| 1318833 | 6/1987 | U.S.S.R. | 73/864.51 |

OTHER PUBLICATIONS

Dempsey et al., "Storage Hopper Sampling Device", IBM Technical Disclosure Bulletin, vol. 21, No. 11, pp. 4369–4370, Apr. 1979.
Mitchell et al., "Continuous Leak Water Sampler", AEC Research and Development Report, Union Carbide Nuclear Company, No. KY–423, pp. 1–3, Nov. 30, 1962.

*Primary Examiner*—Hezron E. Williams
*Assistant Examiner*—Daniel S. Larkin
*Attorney, Agent, or Firm*—Nydegger & Associates

[57] ABSTRACT

A discrete groundwater sampler specifically designed to obtain a low-turbidity groundwater sample directly into the sample transport container, with minimal or no loss of dissolved volatile organic contaminants and no oxidation of dissolved inorganic contaminants, dissolved metals, or dissolved polychlorobiphenyls. The sampler relies on a differential in head-pressure between the fill and exhaust port tubes and an increased sampler can volume to allow overfill of the sample container, causing a flushing of the sample transport container a number of times before the actual sample to be analyzed is actually obtained in the sample transport container. Further, the sampler relies on pressure equilibrium to start and maintain flow through the fill tube; if pressure equilibrium is disturbed or not reached, filling is delayed until the sampler reaches an equilibrium point, usually by lowering it to the desired sampling depth. The sampler is constructed entirely from stainless steel, for non-reactivity with contaminants, ruggedness, and ease of decontamination.

1 Claim, 2 Drawing Sheets

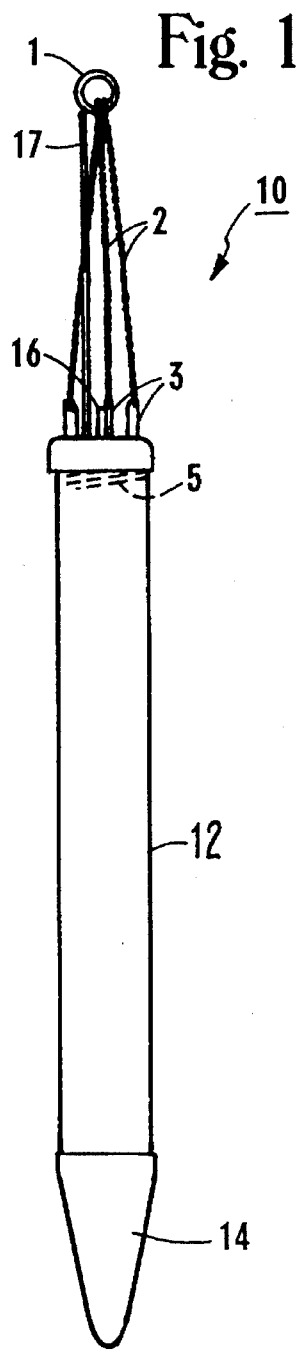
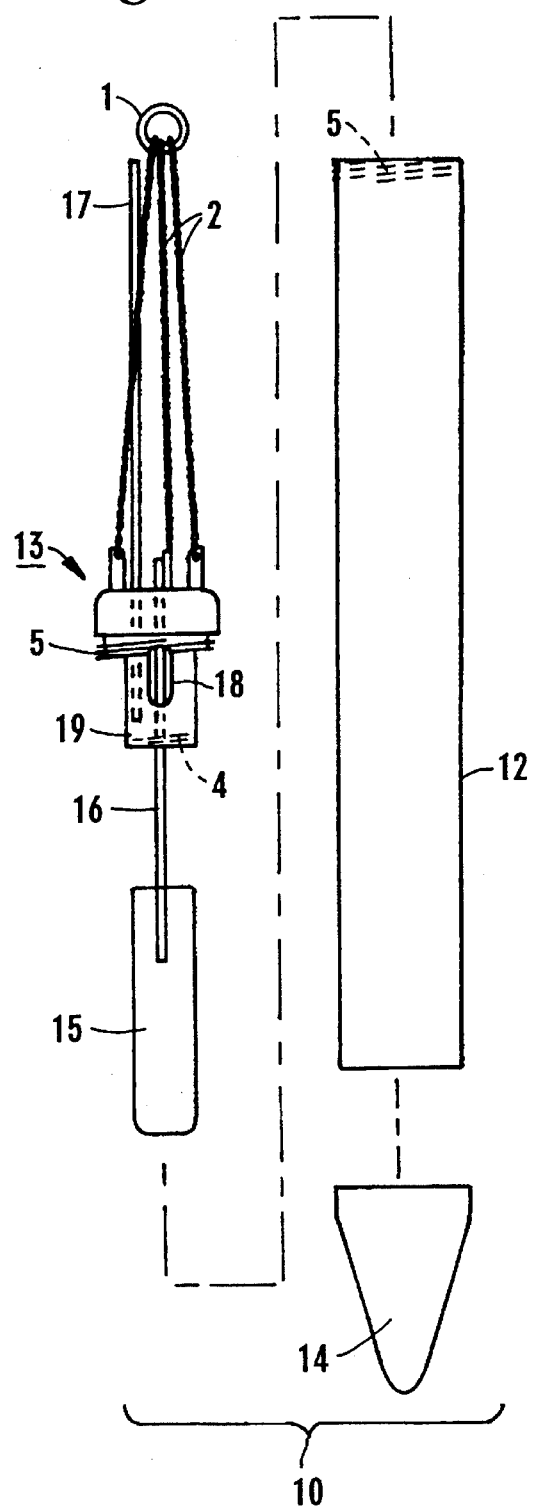

U.S. Patent    Oct. 3, 1995    Sheet 2 of 2    5,454,275
Fig. 3
Fig. 4
Fig. 6
Fig. 5
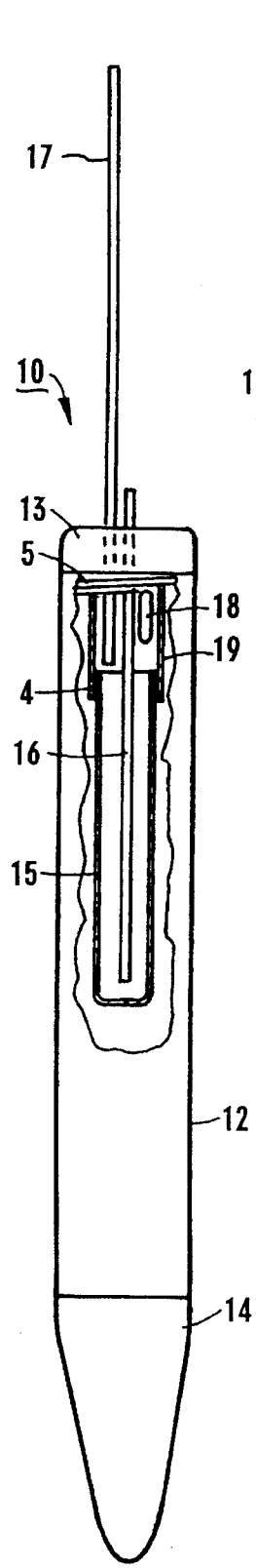
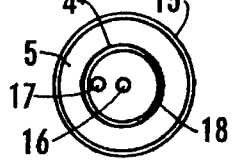
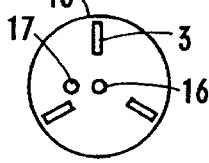
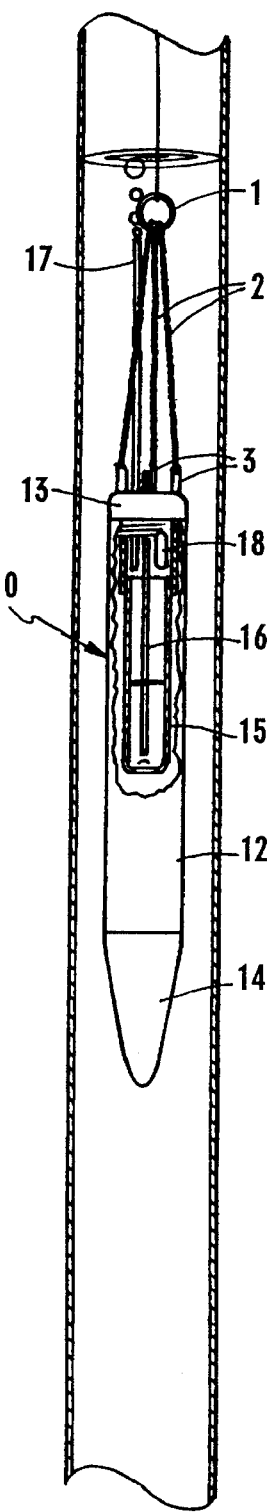

KABIS DISCRETE GROUNDWATER SAMPLER

TECHNICAL FIELD

This invention relates to scientific-sampling equipment, and more particularly to a laminar-flow-type, flushing, discrete groundwater sampler for use in the acquisition of samples of groundwater with low-loss of dissolved volatile organic compounds or of dissolved metals or dissolved polychlorobiphenyls and having low-turbidity for use in groundwater sampling, investigation, reclamation, and remediation.

BACKGROUND ART

Groundwater contamination by a host of water soluble organic and inorganic compounds such as gasoline, polychlorobiphenyls, arsenic, chromium, and nickel present a serious threat to health and human safety. Investigation and remediation are now required by most state and local governments. Integral to the investigation and remediation of groundwater contamination is the sampling of said groundwater to both identify and quantify the pollutants present. There are currently four major methods of obtaining groundwater samples; the open-top bailer, the double-ended COLAWASA sampler, the evacuated-vial sampler, the pressure-pumping sampler, and the Fletcher Sampler. These methods all have the same failings to varying degrees; their action of sample collection causes unusually high turbidity in the obtained water sample, they all require "transfer" of the sampled groundwater to a sample container of some type which results in sample concentration losses and sampling error, and their use requires well purging. The Fletcher sampler is not used for groundwater sampling, but rather for limnolgical and oceanographic sampling.

The open-top bailer is a simple device employing a vertical cylinder into the bottom of which a check-valve of some type is installed. The bailer has a blunt, non-hydrodynamic shape and causes a mixing of the groundwater column, usually resulting in loss of discrete sampling capability and high turbidity in the retrieved sample. The method of operation involves simply lowering the bailer down a groundwater monitoring well past the air-water interface, opening the check valve and allowing the bailer to fill. The bailer is then retrieved to the surface and the groundwater sample transferred by pouring into a sampling container for preservation and transport to a laboratory for identification and quantification. The action of transferring the sample to a sampling container causes splashing and volatilization of volatile organic components resulting in inaccurate quantification of field conditions. Decontamination of the sampling device is not difficult, but it is lengthy.

The double-ended COLAWASA sampler is a 2-meter-long plastic or glass tube, having rubber plugs at either end, attached through their centers with an elastic cord. The COLAWASA sampler has a blunt, non-hydrodynamic shape and causes a mixing of the groundwater column, usually resulting in loss of discrete sampling capability and high turbidity in the retrieved sample. The method of operation involves cocking the two plugs in the open position and simply lowering the COLAWASA sampler down a groundwater monitoring well past the air-water-interface, a tug on the lowering line triggers the plugs at either end to plug the open tube. The COLAWASA sampler is then retrieved to the surface and the groundwater sample transferred by pouring into a sampling container for preservation and transport to a laboratory for identification and quantification. The action of transferring the sample to a sampling container causes splashing and volatilization of volatile organic components resulting in inaccurate quantification of field conditions. Decontamination of the sampling device is difficult and complicated.

The evacuated vial sampler involves an elaborate system of flexible weights, piercing syringe needles, evacuated septum-equipped vials, and a vacuum pump. The sampler operates by evacuating a laboratory-cleaned, septum-equipped glass vial, installing the vial in a cage-like holder which is equipped with a syringe needle and flexible weight system. The entire system is then lowered into a groundwater monitoring well and allowed to hit the bottom of the well. The weights push the vial forward onto the syringe needle, piercing the septum and allowing groundwater to be drawn up into the vial, through the needle, by vacuum pressure. The evacuated vial sampler has a blunt, non-hydrodynamic shape and causes a mixing of the groundwater column, particularly at the bottom of the well, usually resulting in loss of discrete sampling capability and extremely high turbidity in the retrieved sample. The sample is retrieved in its original sampling container, but bubbles in the container usually result in loss of dissolved volatiles. Decontamination of the sampling device is difficult and complicated.

The pressure-pumping sampler involves a down-well pump of some particular operational type. The pressure-pumping sampler has a blunt, non-hydrodynamic shape and causes a mixing of the groundwater column, particularly at the bottom of the well, usually resulting in loss of discrete sampling capability and extremely high turbidity in the retrieved sample. The sample is pumped to the surface where it is captured in an open sampling container. The resultant introduction of finely diffused air during pumping, and the splashing-action of the retrieved groundwater as it is captured in the container guarantee loss of dissolved volatile organic compounds during the sample process. Decontamination of the sampling device is difficult and complicated.

The Fletcher Sampler involves a metal canister into which a 500 milliliter glass bottle sample container, fitted with a ground-glass fritted stopper (when closed), is placed for filling. This canister-type sampler is used primarily for sampling lake or sea water, particularly for chemical oxygen demand studies, but is also commonly used for sewage studies as well. The shape is generally cylindrical, usually 4½- to 5-inches in diameter and 7½- to 8-inches tall, having a flat bottom and a mostly flat top; the entire assembly is generally lowered by way of a thin chain or a nylon cord. The filling mechanism uses a flexible filling tube and a rigid exhaust tube. The flexible filling tube is connected to a rigid tube which pierces through the canister lid, entering the glass neck of the 500 milliliter sample bottle; the sample bottle rests on the bottom of the inside of the canister. The flexible sampling tube is usually strapped to the outside of the canister so as to sample the water closest to the bottom of the lake or sea-bed. As the sampler is lowered to the bottom of the lake or sea-bed, sampling begins, flushing the 500 milliliter sample bottle. This sampler is primarily used for obtaining samples for analysis of the chemical oxygen demand (COD) and biological oxygen demand (BOD) of the water being sampled, and is not generally used for collecting samples of groundwater from groundwater monitoring wells.

DISCLOSURE OF THE INVENTION

The present invention provides a laminar-flow-type, flushing, discrete groundwater sampler for use in the acquisition of samples of groundwater with a very low-loss of dissolved volatile organic compounds or of dissolved metals or dissolved polychlorobiphenyls, and having low-turbidity for use in groundwater sampling, investigation, reclamation, and remediation. The discrete groundwater sampler requires no evacuation, has no moving parts, and relies solely on simply physics for its operation. It is comprises of a stainless steel threaded cap fitted on its top with three suspension lugs, suspension chains connected to a central lift ring, a fill tube, an exhaust tube, a 40 milliliter volatile organic acid sample vial holder, and a sampler can-body fitted with a hydro-dynamic counter weight at the bottom.

An object of the present invention is the provision of an improved method of sampling groundwater which dramatically lowers sample turbidity.

Another object of the present invention is to prevent inorganic contaminant oxidation and dissolved volatile organic contaminant volatilization loss.

A further object of the present invention is to provide for the ability to acquire a depth-discrete groundwater sample of contacting, representative, formational waters.

Still another object of the present invention is to sample directly into a standard 40 milliliter glass sample transport container.

A still further object of the present invention is to provide a sampler which is simple to understand, operate, and decontaminate.

BRIEF DESCRIPTION OF THE DRAWINGS

These and other attributes of the invention will become more clear upon a thorough study of the following description of the best mode for carrying out the invention, particularly when reviewed in conjunction with the drawings, wherein:

FIG. 1 is a side elevational external view of the assembled discrete groundwater sampler and its suspension chains and lifting ring;

FIG. 2 is a side elevational disassembled view of the four major components, the top, the vial, the can, and the counterweight, of the discrete groundwater sampler;

FIG. 3 is a perspective view of the discrete groundwater sampler of the present invention with a portion of the sidewall cutaway to show the internal configuration;

FIG. 4 is a schematic pictogram of the present invention, depicting the in-process filling of both the 40 milliliter vial and the body of the can;

FIG. 5 is a plan and top view of the cap assembly of the discrete groundwater sampler;

FIG. 6 is a plan and bottom view of the cap assembly of the discrete groundwater sampler.

BEST MODE FOR CARRYING OUT THE INVENTION

Referring now to the drawings, wherein like reference numerals designate identical or corresponding parts throughout the several views, FIG. 1 shows the discrete groundwater sampler (10) of the present invention, suspended by a collecting suspension ring (1), connected to each of three suspension chains which are, in turn, connected to the suspension lugs (3), which are machined into the sampler cap assembly (13); the cap assembly is screwed by coarse machine-type threadding (5) into the canister body (12), which is fitted and welded to a solid stainless steel bouyancy counter-weight, having a parabolic, and hydrodynamic groundwater sampler (10) of the present invention. The sampler is comprised of a fill-can (12), a cap assembly (13), a counter-weight (14), and a common (standard) 40 milliliter glass vial (15) threaded into the vial receiver (4). Sampling occurs when groundwater enters the sampler through the filling tube (16) in the cap assembly (13), filling the 40 milliliter glass vial (15), while concurrently, air escapes the sampler through the exhaust tube (17). Filling of the 40 milliliter glass vial (15), held in place by the glass vial holder (19) continues, spilling out of the over-fill ports (18) in the glass vial holder (19), filling the can body (12) of the sampler.

The schematic of FIG. 4 best shows the method of operation of the present invention for sampling groundwater at a discrete depth. The assembled discrete groundwater sampler (10) of the present invention (shown with invisible side wall view) is lowered into a groundwater monitoring well to a pre-determined (desired) depth, suspended by a collecting suspension ring (1) and three stainless steel suspension chains (2), connected to the apex and to the three suspension lugs (3) which are machined into the cap assembly (13). The stainless steel counterweight (14) being of a parabolic, hydrodynamic shape and attached seamlessly to the stainless steel can body, guides the discrete sampler vertically through the water column of the well, creating little or no turbulence. When the assembled discrete groundwater sampler (10) reaches the desired depth, its decent is stopped and an equilibration of pressure differential between the fill tube (16) and the exhaust tube (17) is reached, allowing filing to begin through the fill tube (16). Filling, due to the small diameter of the fill tube (16) and its close proximity to the bottom of the 40 milliliter glass vial (15), assumes both laminar flow and prevents splashing, which prevents volatilization of contaminants from the sampled groundwater. Filling continues in the manner described above until the water level inside the can (12) reaches the bottom exhaust tube (17).

Evaluating Operational Physics Theoretics

The operational preference of variable pressures is known in the science of physics and may be demonstrated through mathematics. The sampler gains its preferential filling capacity from the difference in pressure-head between the fill tube and the exhaust tube. Likewise, the delay in filling until pressure equilibrium has been reached, is achieved by way of the minute difference in pressure over the area of the fill and exhaust tubes, as follows:

$$F = \frac{\rho \cdot G \cdot h}{A} \cong P \qquad 1$$

Where:
F=force
p=density of liquid (water)
G=gravitational constant
h=pressure-head
A=surface area over which force is applied
P=resultant pressure Since for any discrete depth the density of liquid (groundwater) and gravity are constant, the only variables are pressure head and surface area. If surface area is held constant between the fill tube and the exhaust tube, then the final variable to be manipulated is the pressure head (h). From equation (1) above, it can readily be deduced that:

$$P_1 = h_1 \cdot C \quad \wedge \quad P_2 = h_2 \cdot C \qquad 2$$

and that:

$$\text{if } h_1 > h_2 \text{ then } P_1 > P_2 \qquad 3$$

Where:
$P_1$=pressure at fill port
$P_2$=pressure at exhaust port
$h_1$=pressure-head at fill port
$h_2$=pressure-head at exhaust port
C=Constant area, density, and gravity Thus filling proceeds, preferentially, at the point where pressure is greatest, at the fill tube. Laminar flow is induced by the small relative diameter of the fill tube and its close proximity to the bottom of the glass vial. This laminar flow is desirable to prevent volatilization of any dissolved volatile organic contaminants or oxidation of any inorganic contaminants present in the groundwater sample.

Design

Research of the available fabrication materials to construct groundwater samplers, from a sample quality standpoint, revealed only three suitable materials: Corning tempered glass, Teflon, or stainless steel. Corning tempered glass, while having excellent resistance to reaction and degradation characteristics, is severely brittle and extremely expensive for fabrication and materials costs. Teflon, too, has excellent resistance reaction and degradation characteristics, but it is extremely pliable in thin-wall and too brittle in thick-wall applications and is extremely expensive for fabrication and materials costs. Stainless steel has excellent resistance to most chemical attack, is very durable, and in a polished form, very easy to decontaminate. Because of its various forms, it can be molded, spun, machined, and welded, making it the most desirous of the three materials for construction.

The design of the present invention provides for no moving parts and opens easily on a broad rounded thread pattern. The small over-all size of the sampler and the balance in weight from the cap to the can-counterweight assembly provides ease of dextral manipulation.

Thus it can be seen that all of the stated objectives have been achieved.

Obviously, many modifications and variations of the present invention are possible in light of the above teachings. It is therefore understood that, within the scope of the appended claims, the invention may be practiced otherwise than as specifically described.

I claim:

1. A groundwater sampling device comprising in combination:

a cap assembly having suspension lugs machined into that top of the cap assembly;

an exhaust tube and a fill tube passing through the cap assembly;

a vial receiver adapted to receive a glass vial, wherein said vial receiver forms a lower portion of said cap assembly;

a fill can threadedly connected to the cap assembly and adapted to receive samples from an outlet port in the vial receiver;

a parabolical shaped counterweight attached to the lower end of the fill can;

means for suspending the sampling device comprising stainless steel chains connected at one end to a suspension ring and at the other end to the suspension lugs; and means for positioning said fill tube so as to prevent splashing and volatilization of a sample.

* * * * *